US00PP18482P3

(12) United States Plant Patent
Ligonniere

(10) Patent No.: US PP18,482 P3
(45) Date of Patent: Feb. 12, 2008

(54) APPLE TREE NAMED 'DALINIP'

(50) Latin Name: *Malus pumila*
Varietal Denomination: Dalinip

(75) Inventor: Guy Raymond Ligonniere, Angers (FR)

(73) Assignee: SNC Elaris, Angers (FR)

( * ) Notice: Subject to any disclaimer, the term of this patent is extended or adjusted under 35 U.S.C. 154(b) by 124 days.

(21) Appl. No.: 11/348,587

(22) Filed: Feb. 6, 2006

(65) Prior Publication Data

US 2007/0186315 P1 Aug. 9, 2007

(51) Int. Cl.
*A01H 5/00* (2006.01)

(52) U.S. Cl. ..... Plt./161

(58) Field of Classification Search ..... Plt./161
See application file for complete search history.

(56) References Cited

U.S. PATENT DOCUMENTS

PP11,601 P * 10/2000 Fischer et al. ..... Plt./161
2006/0230478 P1 * 10/2006 Hofmann ..... Plt./161

FOREIGN PATENT DOCUMENTS

EP PVR 13782 7/2004

* cited by examiner

*Primary Examiner*—Wendy Haas
(74) *Attorney, Agent, or Firm*—Stratton Ballew PLLC

(57) ABSTRACT

A new and distinct apple tree named 'Dalinip' is disclosed. The new cultivar arose as a whole tree mutation of 'Pinova.' 'Dalinip' is notable for its intense striped coloration and early maturity as compared to its parent and to other known cultivars.

6 Drawing Sheets

Latin name of the genus and species of the plant claimed: *Malus pumila* Mill.
Variety denomination: 'Dalinip'.

BRIEF DESCRIPTION OF THE PHOTOGRAPHS

BRIEF DESCRIPTION OF THE VARIETY

Figure 1:
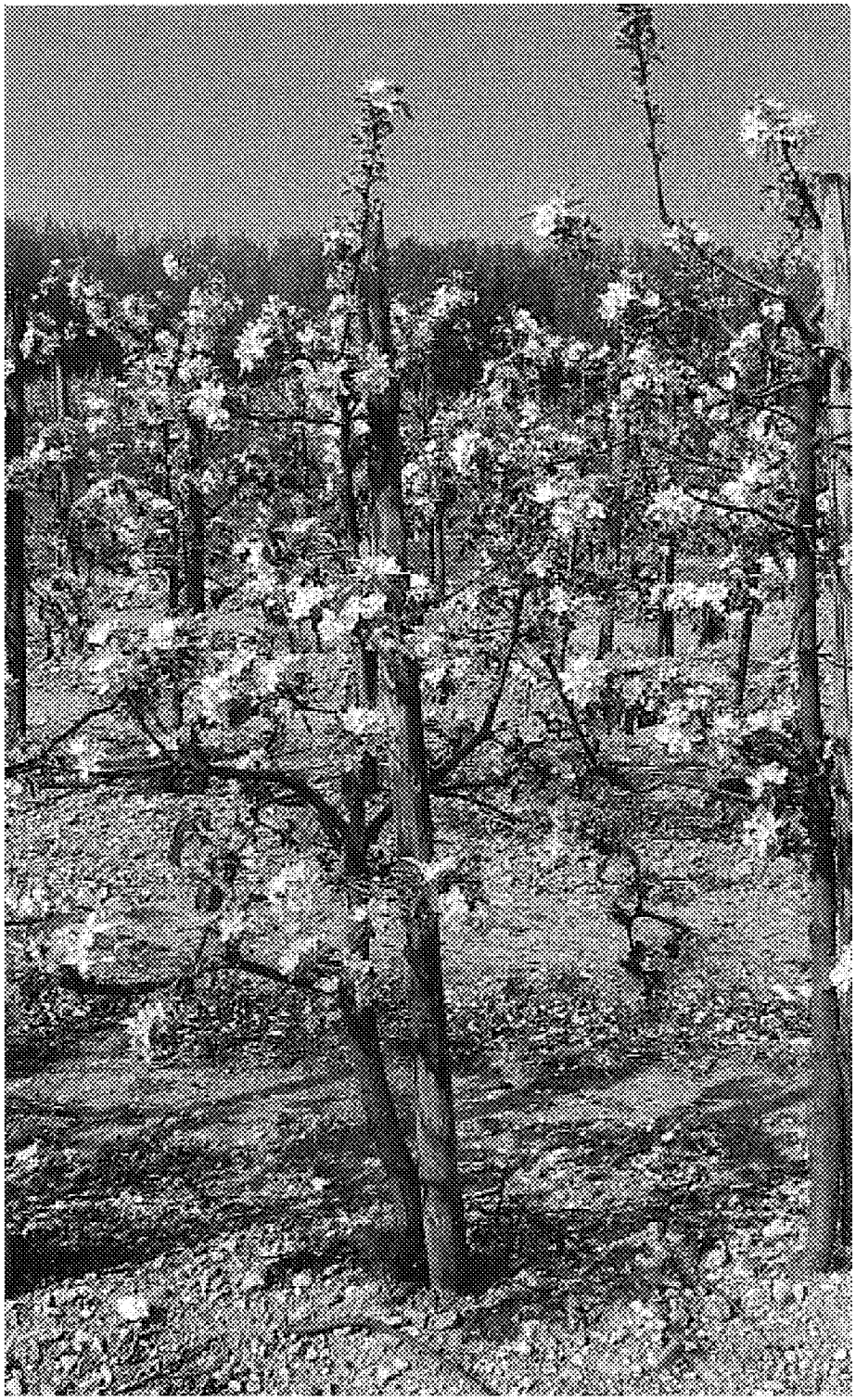
FIG. 1 shows a tree of 'Dalinip' in bloom.
Figure 2:
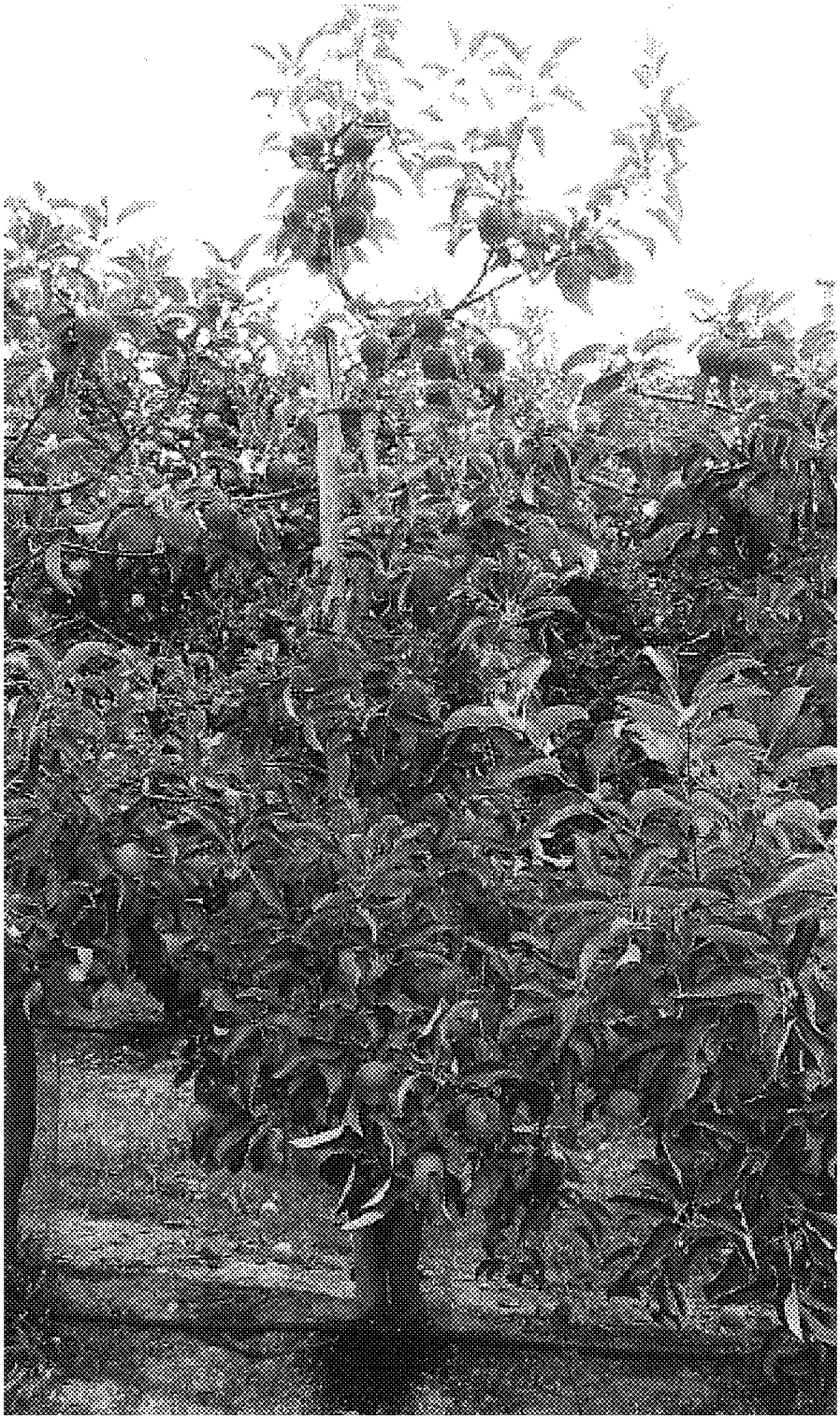
FIG. 2 shows a tree of 'Dalinip' with leaves and fruit.
Figure 3:
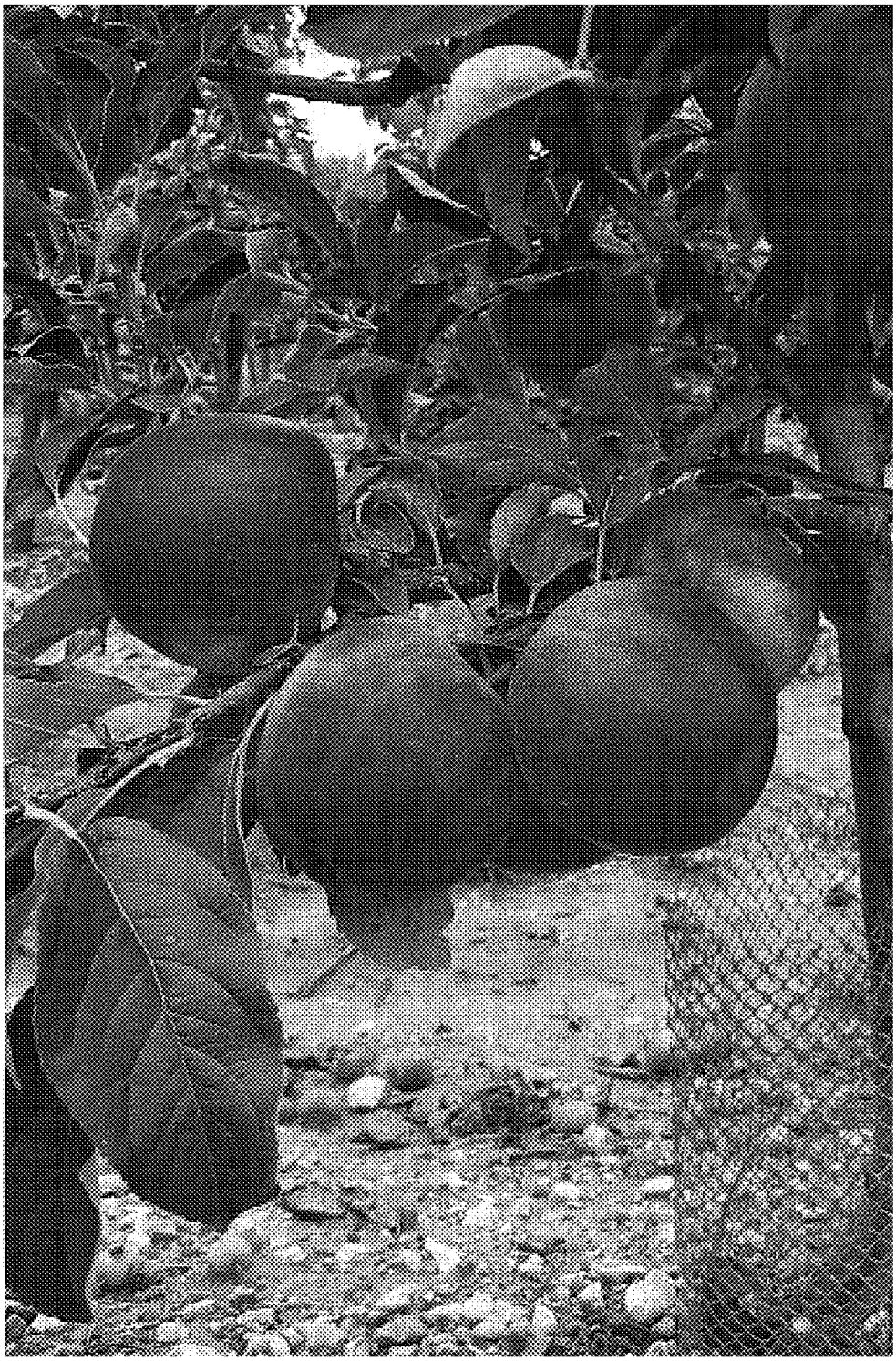
FIG. 3 shows fruit and leaves of 'Dalinip'.
Figure 4:
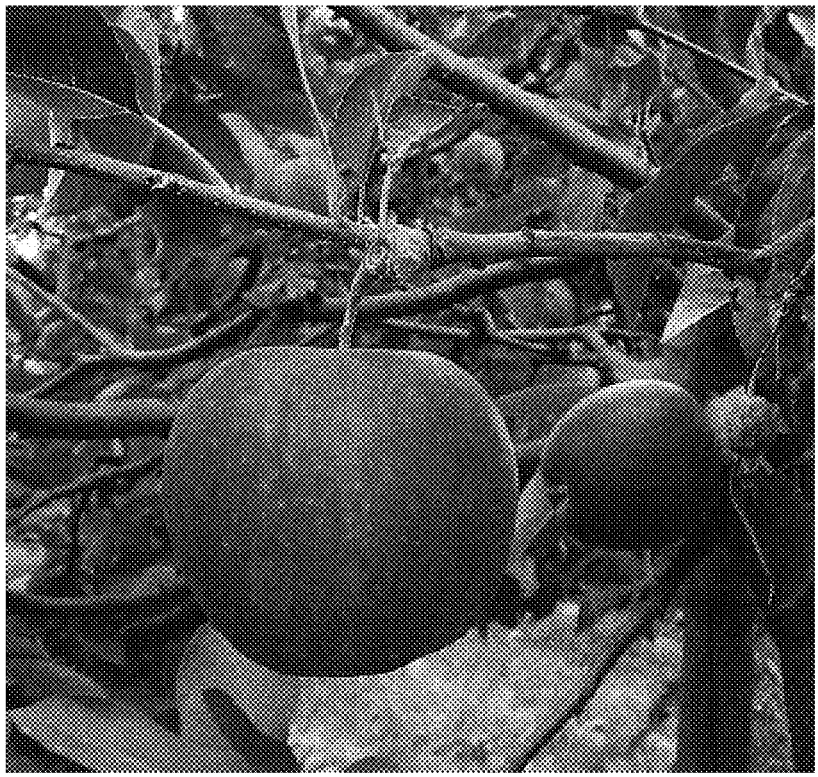
FIG. 4 shows fruit of 'Dalinip'.
Figure 5:
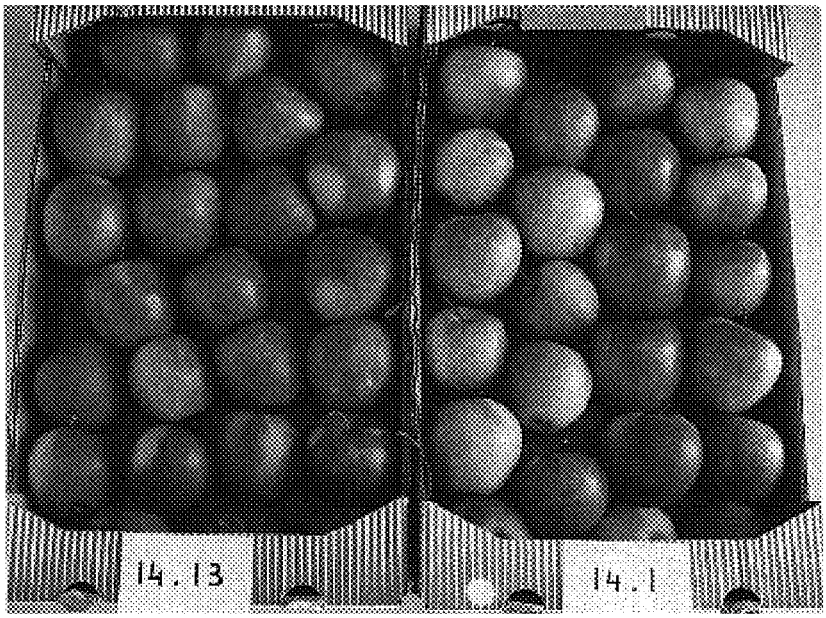
FIG. 5 shows fruit of 'Dalinip' (on the left) as compared to fruit of parent variety 'Pinova'; and, FIG. 6 shows fruit of 'Dalinip' after starch indexing, as compared to fruit of parent variety 'Pinova.'
Figure 6:
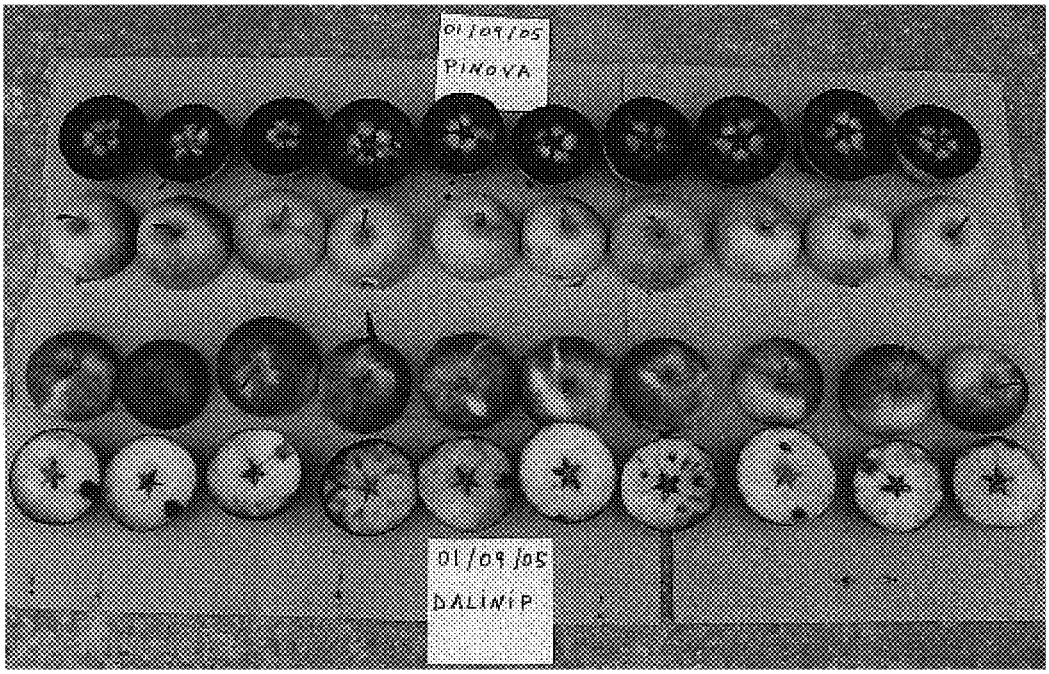

'Dalinip' originated as a whole tree mutation of 'Pinova' (U.S. Plant Pat. No. 11,601). The original tree mutation was discovered during the 1998 harvest in a commercial block of 'Pinova' trees near Lezigne, France, planted on M9 rootstock (not patented) in 1997. The new variety was first asexually propagated by grafting in February 1999 for testing purposes at Doue La Fontaine, France under breeder's reference number MN R37 A72.

The asexually propagated progeny of 'Dalinip' have been found to be homogeneous and stable, retaining the unique characteristics of the original 'Dalinip' tree, and remaining true to type through successive generations of asexual propagation.

'Dalinip' is similar to its parent 'Pinova' in some respects, such as its ability to withstand winter and spring frosts; desirable flavor as a dessert quality fruit; very little or no russeting; no alternate bearing; and good storageability. However, 'Dalinip' is distinguishable from its parent by a number of features. The tree of 'Dalinip' is more dwarfed and compact than 'Pinova', and its branches are smaller than 'Pinova.' While similar in shape and size to the fruit of 'Pinova', The fruit of 'Dalinip' further distinguishes the new variety from its parent. A comparison of the fruit of 'Dalinip' and 'Pinova' is set forth in Table 1 below.

TABLE 1

Comparison of fruit of 'Dalinip' to fruit of parent 'Pinova'

| Characteristic | 'Pinova' | 'Dalinip' |
|---|---|---|
| Maturity Date | Third week of September | First week of September |
| Percentage of foreground color | 25% to 50% | 60% to 80% |
| Pattern of foreground color | Mainly blush with a few stripes | Very prominent stripes |
| Intensity of foreground color | Orange-red | Very intense red with some orange |

DETAILED BOTANICAL DESCRIPTION OF THE VARIETY

The following is a detailed botanical description of 'Dalinip', a new and distinct cultivar of *Malus pumila* Mill., based on observations made of the original tree from 1998 to 2003, and during the 2001 through 2005 growing seasons on specimens of second generation trees planted at Angers, France. All colors are described according to The Royal Horticultural Society Color Chart. It should be understood that the botanical and analytical characteristics described will vary somewhat depending upon cultural practices and climatic conditions, and can vary with location and season. Quantified measurements are expressed as an average of measurements taken from 2 year old trees of the variety planted on M9 rootstock. The measurements of any individual plant, or any group of plants, of the new variety may vary from the stated average.

1. Tree:
   *Vigor.*—Dwarfing; lower vigor than 'Pinova'.
   *Type.*—Spur to ramified; less ramification than 'Pinova'.
   *Habit.*—Upright.
   *Size.*—188 cm high.
   *Trunk.*—Diameter 35 mm at 30 cm above graft union; bark smooth to moderate, grey 201C.
   *Branches.*—Length 39 cm, diameter 16 mm; crotch angle 60° to 80°; brown 200B (fruiting branches about 1 m above graft union).
   *Winter hardiness.*—Similar to 'Pinova'.
   *Chilling requirement.*—Similar to 'Pinova'.
2. Dormant one year old shoot:
   *Pubescence.*—Moderate.
   *Size.*—Length 16.3 cm; thickness 6.7 mm.
   *Color.*—Brown 200B.
   *Internode length.*—Short, 10 mm.
   *Number of lenticels.*—6 lenticels per $cm^2$.
3. Flowers:
   *Bud.*—2 to 3 per spur; conical shape; length 11 mm, diameter 9 mm; red-purple 61A.
   *Flower color* (*balloon stage*).—Purple 77C.
   *Size.*—Diameter 3.8 cm.
   *Petals.*—Usually 5, not touching; ovate with round apex and pointed base; margin smooth; length 21 mm, width 13 mm; upper surface white 155B with purple 76B; lower surface purple 77D.
   *Sepals.*—5 per flower, shape conical, pointed; green 143C.
   *Pedicel.*—Length 2 cm, diameter 1.4 mm; green 142C.
   *Pistil.*—Length 13 mm; yellow-green 145D.
   *Anthers.*—Numerous, average 17 per flower; length 2 mm; pollen present, yellow 4C.
   *Stigma.*—Length 0.5 mm; pale yellow 9C.
   *Style.*—Length 9 mm; yellow-green N144D.
   *Ovary.*—Length 2 mm; green 134A.
   *Bloom period.*—First bloom April 15 in Angers; Full bloom April 20 in Angers (similar to 'Pinova').
4. Leaf:
   *Attitude in relation to shoot.*—Upwards.
5. Leaf blade:
   *Length.*—10.7 cm.
   *Width.*—5.5 cm.
   *Length-width ratio.*—2.
   *Margin.*—Crenate.
   *Shape.*—Oblanceolate; apex acuminate; base oblique.
   *Color.*—Upper surface green 143A; lower surface 143C (in early summer).
6. Petiole: Length 3.5 cm; diameter 1.6 mm; yellow-green 145B.
7. Fruit:
   *Size.*—Diameter 72 mm; 161 g.
   *Quantity per cluster.*—Up to 3 to 4 fruits per cluster.
   *Ratio of height to width.*—0.9.
   *General shape in profile.*—Conical to truncate conical.
   *Position of maximum diameter.*—Top third of fruit.
   *Ribbing.*—Absent.
   *Aperture of eye.*—Closed.
   *Size of eye.*—9.7 mm.
   *Depth of eye basin.*—11.9 mm.
   *Width of eye basin.*—31 mm.
   *Stalk.*—Length 29 cm, diameter 2.1 mm; grey-brown N199D.
   *Stalk cavity.*—Rather flat; depth 7 mm, width 31 mm.
   *Size of lenticels.*—Small to very small, 0.5 mm.
   *Bloom of skin.*—Similar to 'Pinova'.
   *Ground color of skin.*—Yellow 13C.
   *Over color of skin.*—Red stripe on red-orange 42A.
   *Amount of over color.*—60% to 80%.
   *Intensity of over color.*—Bright.
   *Pattern of over color.*—Prominent stripes.
   *Flesh.*—Firm to medium; very juicy; 12° brix at harvest; flesh color yellow 11D.
   *Seeds.*—Usually 5 per fruit; shape truncate ovoid; brown 200D.
   *Harvest date.*—First week of September in Angers (2 weeks before 'Pinova').
   *Harvest window.*—2 picks within 2 weeks.
   *Yield.*—70 fruits harvested per tree (third leaf).

Use: Fresh market.
Resistance to disease: None noted.
Storageability: Similar to 'Pinova'.

I claim:

1. A new and distinct apple tree, substantially as shown and described herein.

* * * * *